United States Patent [19]

Heide et al.

[11] Patent Number: 4,702,930

[45] Date of Patent: Oct. 27, 1987

[54] METHOD OF PRODUCING IMPLANTABLE BONE REPLACEMENT MATERIALS

[75] Inventors: Helmut Heide, Kelkheim; Heinz-Werner Etzkorn, Neu-Anspach; Eva Poeschel, Bad Soden; Helmut Steininger, Neu-Anspach, all of Fed. Rep. of Germany

[73] Assignee: Battelle-Institute e.V., Frankfurt/Main, Fed. Rep. of Germany

[21] Appl. No.: 890,854

[22] PCT Filed: Nov. 4, 1985

[86] PCT No.: PCT/EP85/00586

§ 371 Date: Jul. 18, 1986

§ 102(e) Date: Jul. 18, 1986

[87] PCT Pub. No.: WO86/03977

PCT Pub. Date: Jul. 17, 1986

[30] Foreign Application Priority Data

Dec. 28, 1984 [DE] Fed. Rep. of Germany ....... 3447583

[51] Int. Cl.⁴ .......................... A01N 1/02; B05D 3/06

[52] U.S. Cl. .......................... 427/2; 427/38; 427/309; 623/16; 623/18

[58] Field of Search ................. 427/2, 38, 39, 41, 309; 128/92 C; 428/547; 623/16, 18

[56] References Cited

U.S. PATENT DOCUMENTS 4,623,553 11/1986 Ries et al. .............................. 427/2

FOREIGN PATENT DOCUMENTS 0006544 1/1980 European Pat. Off. .
0023608 2/1981 European Pat. Off. .
0120689 10/1984 European Pat. Off. .
2336913 7/1977 France .

Primary Examiner—Michael R. Lusignan
Attorney, Agent, or Firm—Fisher, Christen & Sabol

[57] ABSTRACT

Metallic implants with a coating of hydroxyl apatite are described. Hot isostatic pressing permits pore-free compaction of the hydroxyl apatite layer and results in firm bonding of the layer on the metallic core. The surface of the layer is partially dehydrated by means of ion bombardment, and a bioactive layer for osteogenesis is produced.

20 Claims, No Drawings

METHOD OF PRODUCING IMPLANTABLE BONE REPLACEMENT MATERIALS

DESCRIPTION

The invention relates to a method of producing implantable bone replacement materials by coating a metallic substrate (core) with a bioactive material on a calcium phosphate basis.

Implants of solid or porous, biocompatible metals or metal compounds are known, as well as bone replacement materials consisting of a plastics or metal matrix with incorporated calcium phosphate ceramic particles or of a dense aluminum oxide ceramic material.

The currently used methods and materials for producing a prosthesis-bone compound which is fully resistant to load are predominantly based on purely mechanical anchorages achieved by screwing or nailing, or on purely mechanically acting cementing, e.g., of a prosthesis shaft in an artificially produced cavity in the bone. These mechanical anchorages often cause inadmissibly high stresses in the bone bed which lead to atrophy of the bone region affected and thus to later loosening of the prosthesis.

The stability of the prosthesis anchorage is also dependent on the chemism of the materials used. The currently used biocompatible metals as well as the biostable oxide ceramics and the tissue-neutral polymer materials are, without exception, recognized by the bone as foreign bodies and thus remain encapsulated by tissue. This phenomenon, which is to be regarded as a first stage of rejection, in the case of permanently loaded prosthesis parts leads to widening of the connective-tissue membrane in the bone-implant boundary zone and to loosening and later rejection of the implanted material.

A different physiological behavior is shown by the bioactive implant materials, e.g. the bioactive calcium phosphate ceramics, which are more or less biodegradable, i.e. resorbable, depending on their composition. In the course of their chemical decomposition, these materials release materials to the surrounding tissue which do not disturb bone formation but, on the contrary, permit or even stimulate calcification of the bone tissue immediately on the alloplastic surface.

The term "bioactive" implies a specific chemical reaction of the material with the bone cells. Although this property is desirable for direct bone implant formation, it excludes the sole use of these materials for a permanent implant. An additional drawback consists in their relatively low mechanical strength, which is not sufficient for highly loaded endoprotheses. Therefore, the above-mentioned plastics were developed from resorbable plastic with incorporated bioceramic particles; the mechanical strength of these materials is, however, still insufficient, in particular after resorption of the ceramic component.

It is also known to coat a metallic prosthesis core with bioactive substances, e.g. with at least one enamel or enamel-like carrier layer into which the bioactive materials are then incorporated. In this case the serious drawback of the application of an enamel coating is accepted in order to achieve a satisfactory bond strength, although this enamel coating is incompatible with the bioceramic material and inavoidably results in tissue-incompatible decomposition products. It is not recognized that a firm bond between bioceramic and metal can also be achieved without enamel or enamel-like intermediate layers.

To produce bone or dental prostheses, it is known to apply a coating of a eutectoi of tricalcium phosphate and tetracalcium phosphate by means of a flame or plasma spraying device or to coat the entire metallic prosthesis with dense and porous ceramic material. For this pupose, tissue-incompatible bonding agents are required, as otherwise no sufficient bond between the coating and the implants can be reached.

In the case of a further known bone replacement material, calcium phosphate particles are incorporated into a solid metal core in the form of a single layer. These calcium phosphate particles have from the beginning a composition of $CaO:P_2O_5$ between 3:1 and 4:1. The coating of prosthesis metals with such bioactive and biocompaticle materials is problematic, as bonding problems between the metal substrate and the coating material result, e.g., from different thermal expansion coefficients of the material and from mechanical incompatibilities between the materials. In addition, the surface materials are contaminated with unphysiological chemical impurities from the substrate or from the environment. The pure coating materials show insufficient mechanical stability. Direct sintering of calcium phosphate ceramic onto compact prosthesis shafts is also impossible because of bonding problems and because of the differences in thermal expansion behavior. As the suitable calcium phosphate phases cannot be dense sintered without application of pressure, there is the risk of metal ions penetrating through the prosthesis coating into the bone bed. Such coatings therefore have been found in the past to be unsuited from the points of view of both materials technology and biology.

The object of the invention is to develop a method of producing firmly adhering bioactive coatings without any detrimental change of the chemical nature and thus of the biological behavior.

According to the invention, this object is reached by applying a porous layer of hydroxyl apatite onto the metallic core and compacting it by hot isostatic pressing, the prssure and the temperature being adjusted such that dehydration of hydroxyl apatite is avoided, and by subsequently dehydrating the hydroxyl apatite layer partially by ion bombardment.

The hot isostatic pressing is advantageously carried out at pressures above 1 kbar and temperatures above 400° C. The hydroxyl apatite layer is advantageously dehydrated down to a depth of 0.1 to 1.0 $\mu$m, preferably 0.5 $\mu$m.

Prior to being coated with hydroxyl apatite, the metallic core is advantageously pretreated by chemical and/or physical methods, preferably by etching, sputtering, plasma spraying and/or ion implantation.

Prior to hot isostatic pressing, the porous hydroxyl apatite layer is advantageously subjected to cold isostatic pressing. The cold isostatic pressing is advantageously carried out by using a slip and an elastic container, which is preferably made of rubber.

Advantageously the hot isostatic pressing is carried out in a glass container and, in order to prevent reactions with the hydroxyl apatite layer, advantageously an inert barrier material, preferably graphite or boron nitride, is used.

The compacted hydroxyl apatite coating is advantageously cleaned by wet chemical and/or physical methods, preferably by etching and/or sputtering.

The material produced by the method according to the invention is characterized by reduced bioactivity in its mass, but is made bioactive in its boundary layer down to a maximum depth of 1 μm. As a result, it is resorbable only in a thin defined surface region. According to the invention, the chemical and mechanical stability of the tissue-compatible metals is utilized, and these very important properties are combined with the bioactivity of the coating material which is responsible for the formation of new bone material. The non-resorbable hydroxyl apatite, which also occurs in natural bone, is dehydrated by high-energy ion bombardment and thus converted in particular into the resorbable tricalcium phosphate. This conversion of hydroxyl apatite takes place mainly in the surface region. The resorbable calcium phosphate phases are thus formed without a sintering process.

The metallic core is preferably made of titanium. Also other tissue-compatible materials are suited. Such a solid metal core is then provided with a porous layer of hydroxyl apatite by means of a slip. The coated metal core is then subjected to a HIP (Hot Isostatic Pressing) treatment at pressures above 1 kbar and at temperatures above 400° C. This results in pore-free compaction of the coating and in its firm bonding to the metallic substrate. In addition to $H_2O$ decomposition pressure of the hydroxyl apatite is compensated by the high internal pressure of the HIP apparatus plant, so that the hydroxyl apatite does not decompose. Subsequently, the cleaned surface of the implant is dehydrated by intensive ion bombardment down to a depth of about 0.1 to 0.5 μm; this results in formation of a lattice structure similar to that of tricalcium phosphate, which shows high bioactivitty and serves as starter layer for osteogenesis.

It is advantageous to clean the surface of the metallic core prior to coating by conventional chemical and/or physical methods. It is possible to use, e.g., etching, sputtering, plasma spraying and/or ion implantation for this purpose. The bond strength between the calcium phosphate layer and the metallic substrate is further increased by a cold isostatic pressing treatment prior to hot isostatic pressing. This is preferably effected by using a slip and an elastic container, e.g. of rubber. Hot isostatic pressing can be performed in a glass container. To prevent reactions between the container material and the coating, a barrier material is used. Suitable barrier materials are all inert substances, in particular graphite or boron nitride.

We claim:

1. Method of producing implantable bone replacement materials by coating a metallic core with a bioactive material, comprising: applying a porous layer of hydroxyl apatite onto the metallic core and compacting it by hot isostatic pressing, the pressure and the temperature being adjusted such that dehydration of hydroxyl apatite is prevented; and subsequently partially dehydrating the hydroxyl apatite by ion bombardment.

2. Method as claimed in claim 1 wherein hot isostatic pressing is carried out at pressures above 1 kbar and temperatures above 400° C.

3. Method as claimed in claim 1 or claim 2 wherein the hydroxyl apatite layer is dehydrated down to a depth of 0.1 to 0.1 μm.

4. Method as claimed in claim 3 wherein the dehydration is down to a depth of 0.5 μm.

5. Method as claimed in claim 3 wherein, prior to being coated with hydroxyl apatite, the metallic core is pretreated by chemical and/or physical methods.

6. Method as claimed in claim 5 wherein the metallic core is pretreated by etching, sputtering, plasma spraying and/or ion implantation.

7. Method as claimed in claim 5 wherein prior to hot isostatic pressing, the porous hydroxyl apatite layer is subjected to cold isostatic pressing.

8. Method as claimed in claim 7 wherein cold isostatic pressing is carried out by using a slip and an elastic container.

9. Method as claimed in claim 8 wherein the elastic container is made of rubber.

10. Method as claimed in claim 7 wherein hot isostatic pressing is carried out in a glass container and wherein, in order to prevent reactions with the hydroxyl apatite layer, an inert barrier material, preferably graphite or boron nitride, is used.

11. Method as claimed in claim 10 wherein the compacted hydroxyl apatite coating is cleaned by wet chemical and/or physical methods.

12. Method as claimed in claim 11 wherein the cleaning is done by etching and/or sputtering.

13. Method as claimed in claim 1 wherein, prior to being coated with hydroxyl apatite, the metallic core is pretreated by chemical and/or physical methods.

14. Method as claimed in claim 12 wherein the metallic core is pretreated by etching, sputtering, plasma spraying and/or ion implantation.

15. Method as claimed in claim 1 wherein prior to hot isostatic pressing, the porous hydroxyl apatite layer is subjected to cold isostatic pressing.

16. Method as claimed in claim 15 wherein cold isoatatic pressing is carried out by using a slip and an elastic container.

17. Method as claimed in claim 16 wherein the elastic container is made of rubber.

18. Method as claimed in claim 1 wherein hot isostatic pressing is carried out in a glass container and wherein, in order to prevent reactions with the hydroxyl apatite layer, an inert barrier material, preferably graphite or boron nitride, is used.

19. Method as claimed in claim 1 wherein the compacted hydroxyl apatite coating is cleaned by wet chemical and/or physical methods.

20. Method as claimed in claim 19 wherein the cleaning is done by etching and/or sputtering.

* * * * *